US012357312B2

(12) United States Patent
Wan et al.

(10) Patent No.: US 12,357,312 B2
(45) Date of Patent: Jul. 15, 2025

(54) ANVIL AND DELIVERY SYSTEM ASSEMBLY WITH AUTOMATIC RETAINING SUTURE RELEASE

(71) Applicant: Covidien LP, Mansfield, MA (US)

(72) Inventors: Yanli Wan, Shanghai (CN); Yishuai Xu, Shanghai (CN); Jinhang Liu, Shanghai (CN); Yanjun Jiao, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/563,122

(22) PCT Filed: May 24, 2021

(86) PCT No.: PCT/CN2021/095510
§ 371 (c)(1),
(2) Date: Nov. 21, 2023

(87) PCT Pub. No.: WO2022/246600
PCT Pub. Date: Dec. 1, 2022

(65) Prior Publication Data
US 2024/0237985 A1    Jul. 18, 2024

(51) Int. Cl.
*A61B 17/115*    (2006.01)
*A61B 17/00*     (2006.01)

(52) U.S. Cl.
CPC . *A61B 17/1155* (2013.01); *A61B 2017/00477* (2013.01)

(58) Field of Classification Search
CPC ............. A61B 17/07207; A61B 17/1155
See application file for complete search history.

(56) References Cited

U.S. PATENT DOCUMENTS

| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| AU | 2016 210 627 A1 | 8/2016 |
| CA | 908529 A | 8/1972 |

(Continued)

OTHER PUBLICATIONS

International Search Report for Application No. PCT/CN2021/095510 dated Jan. 28, 2022.

(Continued)

*Primary Examiner* — Nathaniel C Chukwurah (57) ABSTRACT

An anvil and delivery system assembly includes an anvil and a delivery system assembly. The delivery system includes a flexible guide member, an adapter, a tie down suture, and a retaining suture. The guide member is coupled to the center rod with the adapter. The tie down suture is secured to the adapter and to the anvil head to retain the anvil head in the tilted position during anvil delivery. The retaining suture is coupled to the anvil head via the tie down suture such that release of the tie down suture automatically releases the retaining suture from the anvil head.

20 Claims, 9 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | |
|---|---|---|
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 * | 12/2013 | Milliman ............ A61B 17/115 227/19 |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |

(56) References Cited

U.S. PATENT DOCUMENTS

| | | | |
|---|---|---|---|
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,517,070 B2 * | 12/2016 | Mulreed ............. A61B 17/115 |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,855,045 B2 * | 1/2018 | Williams ............. A61B 17/1155 |
| 9,861,367 B2 * | 1/2018 | Williams ............. A61B 17/068 |
| 9,861,368 B2 | 1/2018 | Racenet et al. |
| 9,867,619 B2 * | 1/2018 | Williams ............. A61B 17/064 |
| 9,883,862 B2 | 2/2018 | Rebuffat et al. |
| 9,907,600 B2 | 3/2018 | Stulen et al. |
| 9,974,536 B2 * | 5/2018 | Sgroi, Jr. ............ A61B 17/0469 |
| 10,039,549 B2 | 8/2018 | Williams |
| 10,085,744 B2 | 10/2018 | Williams et al. |
| 10,085,756 B2 * | 10/2018 | Williams ......... A61B 17/00234 |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,828,026 B2 * | 11/2020 | Williams ............. A61B 17/1152 |
| 10,898,196 B2 | 1/2021 | Sapienza et al. |
| 11,197,676 B2 * | 12/2021 | Kollar .................. A61B 17/068 |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |

(56) References Cited

U.S. PATENT DOCUMENTS

| | | |
|---|---|---|
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2017/0000475 A1 | 1/2017 | Sgroi, Jr. et al. |
| 2017/0128068 A1 | 5/2017 | Zhang et al. |

FOREIGN PATENT DOCUMENTS

| | | |
|---|---|---|
| CA | 2805365 A1 | 8/2013 |
| CN | 100376348 C | 3/2008 |
| CN | 102014768 B | 1/2013 |
| CN | 104039244 A | 9/2014 |
| CN | 104042288 A | 9/2014 |
| CN | 101647720 B | 10/2014 |
| CN | 104367360 A | 2/2015 |
| CN | 110652327 A | 1/2020 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004032766 A2 | 4/2004 |
| WO | 2004047654 A2 | 6/2004 |
| WO | 2008107918 A1 | 9/2008 |
| WO | 2019130087 A1 | 7/2019 |

OTHER PUBLICATIONS

Written Opinion for Application No. PCT/CN2021/095510 dated Jan. 28, 2022.

Supplementary European Search Report for EP Application No. 21 94 2189 mailed Jan. 13, 2025 (11 pages).

* cited by examiner

ANVIL AND DELIVERY SYSTEM ASSEMBLY WITH AUTOMATIC RETAINING SUTURE RELEASE

FIELD

The technology is generally related to anvil assemblies for surgical stapling devices and, more particularly, to an anvil and delivery system assembly for delivering an anvil to an anastomotic site prior to a surgical anastomosis procedure.

BACKGROUND

Trans-oral delivery systems for delivering an anvil to a surgical site, e.g., the stomach, prior to performance of a surgical anastomosis procedure are known. Typically, the delivery system includes flexible guide member that is releasably coupled to a center rod of the anvil, a retaining suture that is coupled to an anvil head of the anvil, and a tie down suture that is secured to the anvil head and to an adapter that is coupled to the flexible guide member to secure the anvil head in a tilted position.

When the anvil is delivered trans-orally to an anastomotic site, e.g., the stomach, the guide member is fed through the esophagus into the stomach and through openings in the stomach and the abdominal wall. When the guide member exits through the opening in the abdominal wall, the guide member is grasped by a clinician and pulled through the abdominal wall to pull the anvil through the esophagus and into the stomach. As the anvil is being pulled into the stomach, the clinician grasps the retaining suture which extends from the mouth of the patient and may be used by a clinician to dislodge the anvil if the anvil becomes stuck during delivery of the anvil and/or to retrieve the anvil in the event of a patient emergency, e.g., cardiac arrest.

After the anvil is delivered to the anastomotic site, the flexible guide member is disconnected from the center rod of the anvil by cutting the tie down suture, and the anvil is coupled to a circular stapling device to perform the anastomosis procedure. In certain situations, the retaining suture may become trapped between the anvil and the circular stapling device and subsequently stapled to the anastomotic site.

A continuing need exists in the art for an anvil and delivery system assembly that ensures that the retrieval suture does not interfere with formation of the anastomosis.

SUMMARY

Aspects of this disclosure are directed to an anvil and delivery system assembly that can be used to delivery an anvil to a surgical site during a surgical anastomosis procedure. The delivery system includes a flexible guide member, an adapter, a tie down suture, and a retaining suture. The tie down suture is secured to an anvil head of the anvil to retain the anvil head in a tilted position during anvil delivery. The retaining suture is coupled to the anvil head via the tie down suture such that release of the tie down suture automatically releases the retaining suture from the anvil head.

Aspects of this disclosure are directed to an anvil and delivery system assembly including an anvil and a delivery system. The anvil includes an anvil head and a center rod. The anvil head is secured to the center rod by a pivot member and is movable between a first tilted position, an operative position, and a second tilted position. The delivery system includes a flexible guide member, an adapter, a tie down suture, and a retaining suture. The flexible guide member is coupled to the center rod of the anvil with the adapter. The tie down suture is secured to the anvil head and to the adapter to retain the anvil head in the first tilted position. The retaining suture is secured to the anvil head via the tie down suture such that release of the tie down suture from the anvil head automatically releases the retaining suture from the anvil head.

In aspects of this disclosure, the anvil head includes a body defining first and second openings, and the tie down suture extends through the first opening in the anvil head and from the second opening of the anvil head to secure the tie down suture to the anvil head.

In some aspects of this disclosure, the body of the anvil head defines a third opening, and the retaining suture extends into the third opening, is wound about the tie down suture, and extends back through the third opening to secure the retaining suture to the anvil head.

In certain aspects of this disclosure, the adapter includes a distal connector that is received within the flexible guide member to frictionally secure the adapter to the flexible guide member.

In aspects of this disclosure, the tie down suture includes first and second ends that are compressed between the distal connector of the adapter and the flexible guide member.

In some aspects of this disclosure, the delivery system includes a reel, and a portion of the retaining suture is supported within the reel and can be selectively fed from the reel.

In certain aspects of this disclosure, the distal connector includes ribs that engage the flexible guide member to secure the adapter within the flexible guide member.

In aspects of this disclosure, the adapter includes a proximal connector that is received within the center rod of the anvil.

In some aspects of this disclosure, the center rod includes a distal portion that is coupled to the anvil head by the pivot member and a proximal portion that includes flexible legs that define a longitudinal bore.

In certain aspects of this disclosure, the longitudinal bore is dimensioned to releasably receive a trocar of a stapling device to releasably secure the anvil to the stapling device.

Other aspects of this disclosure are directed to an anvil and delivery system assembly that includes an anvil and a delivery system. The anvil includes an anvil head and a center rod. The anvil head is secured to the center rod by a pivot member and is movable between a tilted position and an operative position. The delivery system includes a flexible guide member, a tie down suture, and a retaining suture. The flexible guide member is coupled to the center rod of the anvil. The tie down suture is secured to the anvil head and to the flexible tube to retain the anvil head in the tilted position. The retaining suture is secured to the anvil head via the tie down suture such that release of the tie down suture from the anvil head automatically releases the retaining suture from the anvil head.

In aspects of this disclosure, the proximal connector of the adapter includes a rib that is received between the flexible legs of the center rod to prevent rotation of the center rod in relation to the adapter.

Other features of the disclosure will be appreciated from the following description.

BRIEF DESCRIPTION OF DRAWINGS

Various aspects of the disclosure are described herein below with reference to the drawings, wherein.

DETAILED DESCRIPTION

The disclosed anvil and delivery system assembly will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary fashion, while the term "distal" is used generally to refer to that portion of the device that is farther from the clinician during use of the device in its customary fashion. In addition, the term "clinician" is used generally to refer to medical personnel including doctors, nurses, and support personnel.

This disclosure is directed to an anvil and delivery system assembly that can be used to delivery an anvil to a surgical site during a surgical anastomosis procedure. The anvil and delivery system assembly includes an anvil and a delivery system. The anvil an anvil head that is coupled to a center rod by a pivot member that facilitates pivotal movement of the anvil head in relation to the center rod between tilted and operative positions. The delivery system includes a flexible guide member, an adapter, a tie down suture, and a retaining suture. The guide member is coupled to the center rod with the adapter. The tie down suture is secured to the adapter and to the anvil head to retain the anvil head in the tilted position during anvil delivery. The retaining suture is coupled to the anvil head via the tie down suture such that release of the tie down suture automatically releases the retaining suture from the anvil head.

Figures 1, 1A:
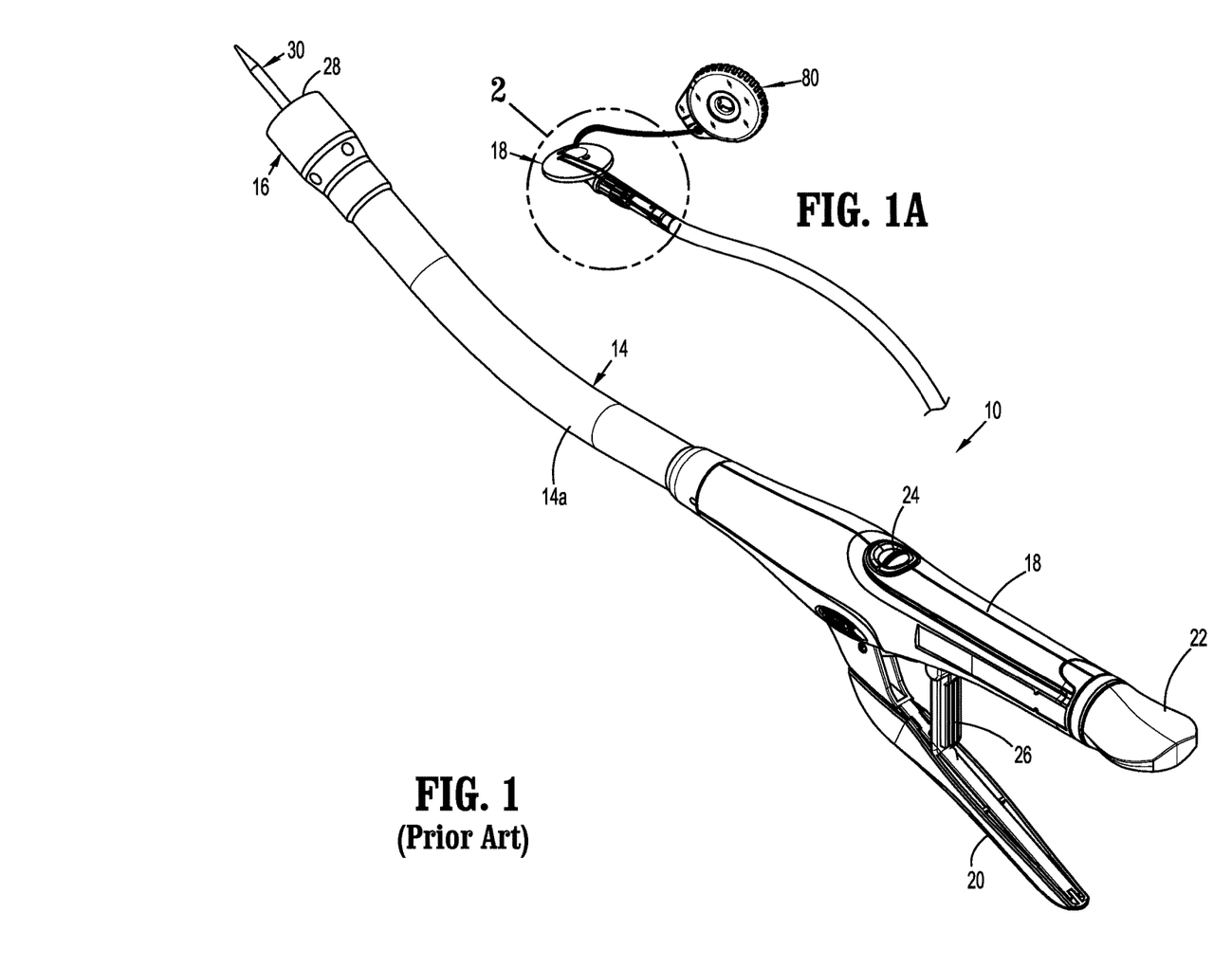
FIG. 1 is a side perspective view of a Prior Art circular stapling device.
FIG. 1A is a side perspective view of an anvil and delivery system assembly including anvil for use with the stapling device of FIG. 1 with an anvil head of the anvil in a tilted position.

FIG. 1 illustrates a surgical stapling device that is configured for use with an anvil having a tiltable anvil head. Although the anvil and delivery system assembly of the disclosure will be described with reference to a surgical stapling device 10, it is envisioned that the anvil assemblies and delivery systems may be modified for use with alternative surgical stapling devices.

The surgical stapling device 10 includes a handle assembly 12, an elongated body 14 having a curved elongate outer tube 14a, a shell assembly 16, and an anvil 18. The length, shape and/or the diameter of the body portion 14 and the shell assembly 16 may be modified to suit a particular surgical procedure.

The handle assembly 12 includes a stationary handle 18, a firing trigger 20, a rotatable approximation knob 22, and an indicator 24. A trigger lock 26 is coupled to the handle assembly 12 by a pivot member (not shown) and is manually movable from an unlocked position to a locked position to prevent inadvertent firing of the stapling device 10. The indicator 24 is positioned on the stationary handle 18 and includes indicia, e.g., color coding, alpha-numeric labeling, etc., to identify to a clinician when the stapling device 10 is approximated and is in a fire-ready position.

The shell assembly 16 of the tool assembly includes a staple cartridge 28 that supports staples (not shown). The stapling device 10 includes a trocar assembly 30 that extends from the elongate body 14 and through the shell assembly 16. The trocar assembly 30 is adapted to be releasably coupled to the anvil 18. For a more detailed discussion of an exemplary surgical stapling device, please refer to U.S. Pat. No. 7,364,060.

Figure 2:
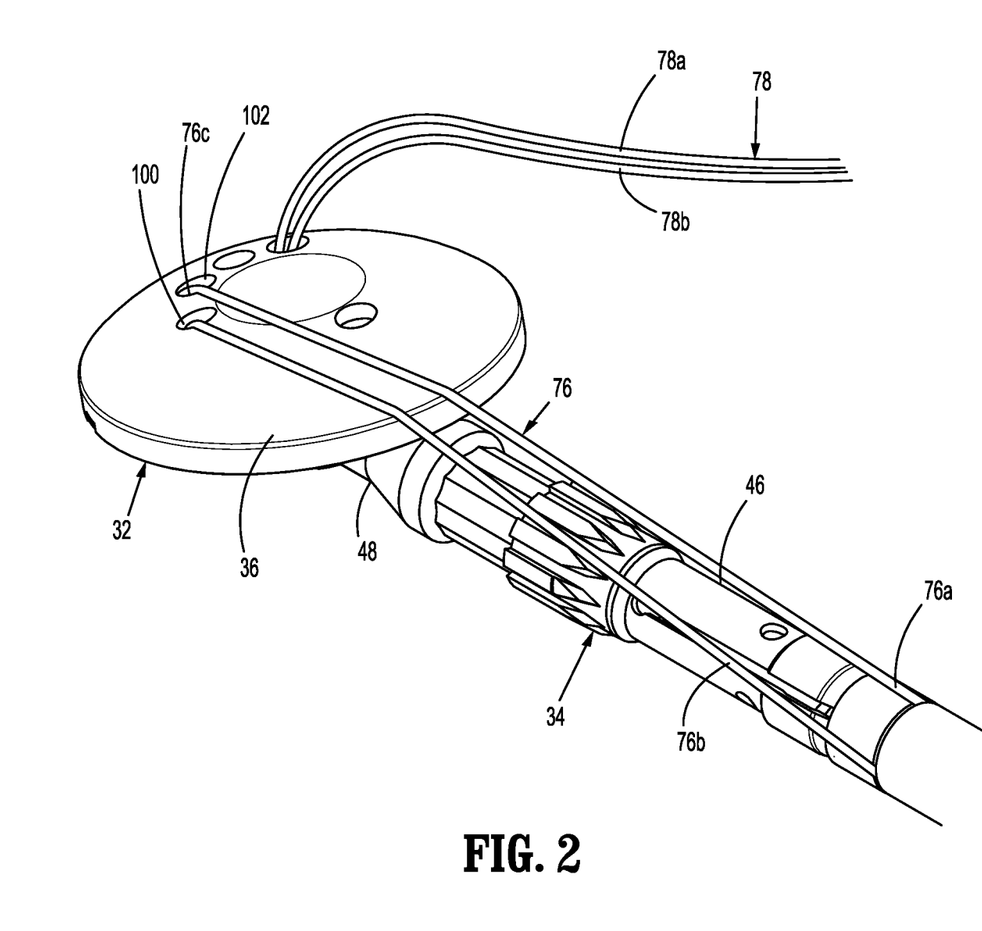
FIG. 2 is an enlarged view of the indicated area of detail shown in FIG. 1.
Figure 3A:
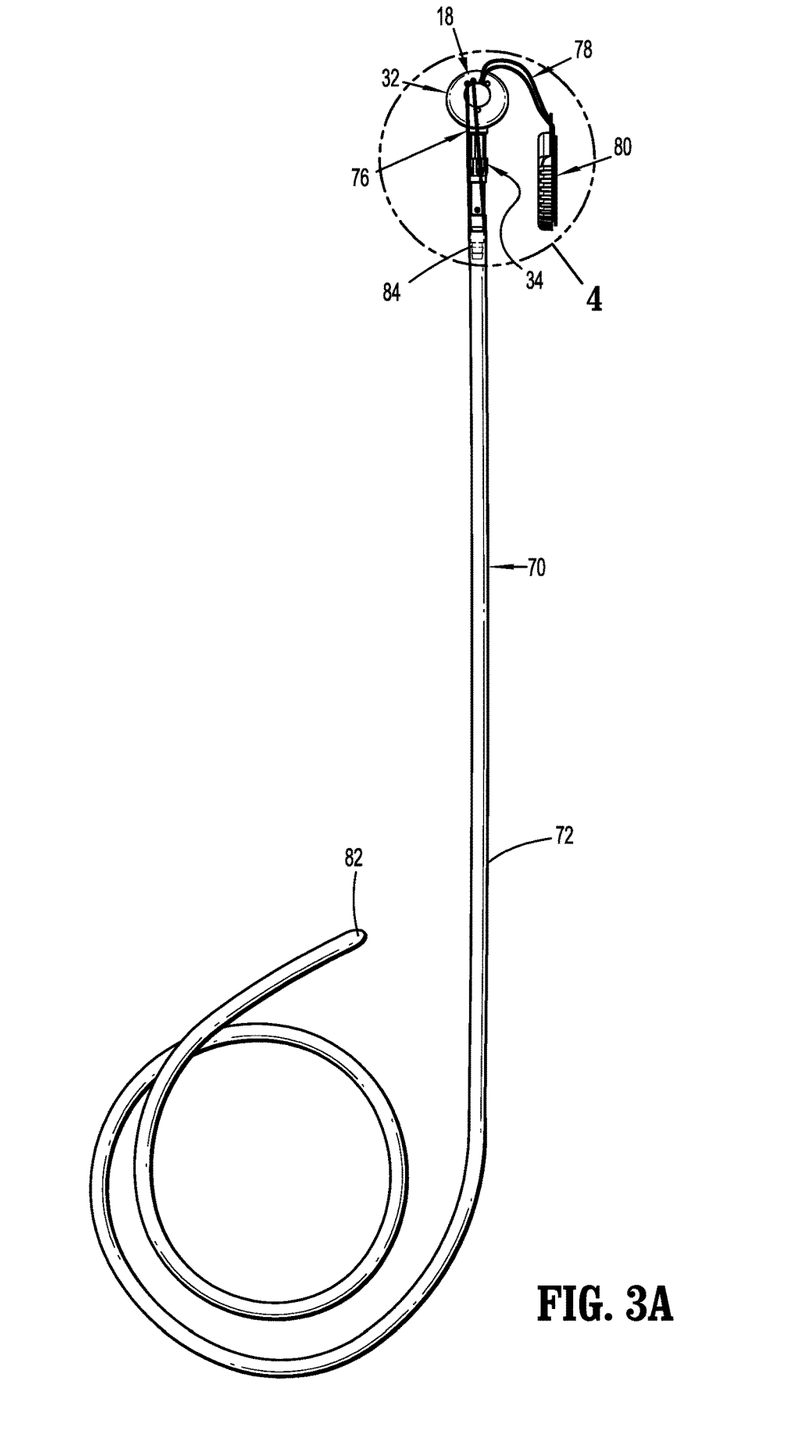
FIG. 3A is a side perspective view of the anvil and anvil delivery system shown in FIG. 1 with the anvil delivery system coupled to the anvil and the anvil head assembly of the anvil in the tilted position.
Figure 3B:
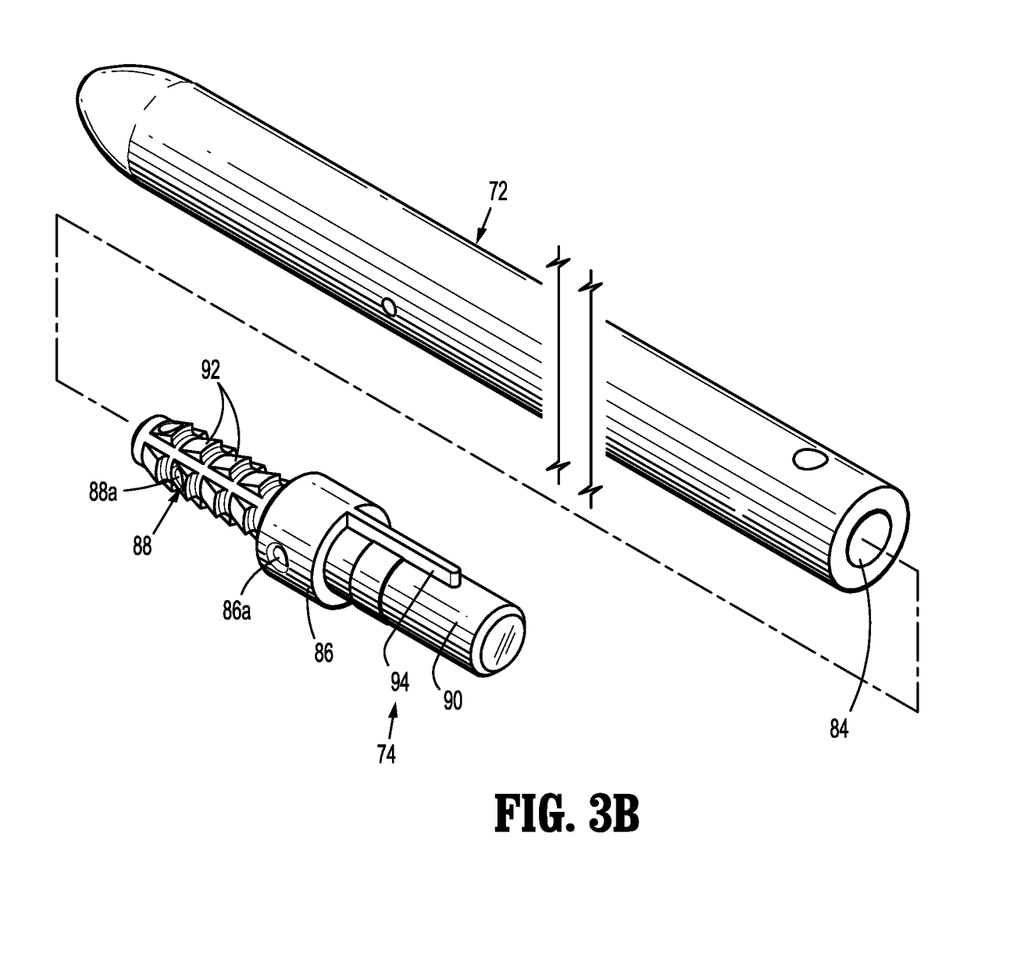
FIG. 3B is aside perspective view of an adapter and flexible guide member of the anvil delivery system shown in FIG. 1.
Figure 4:
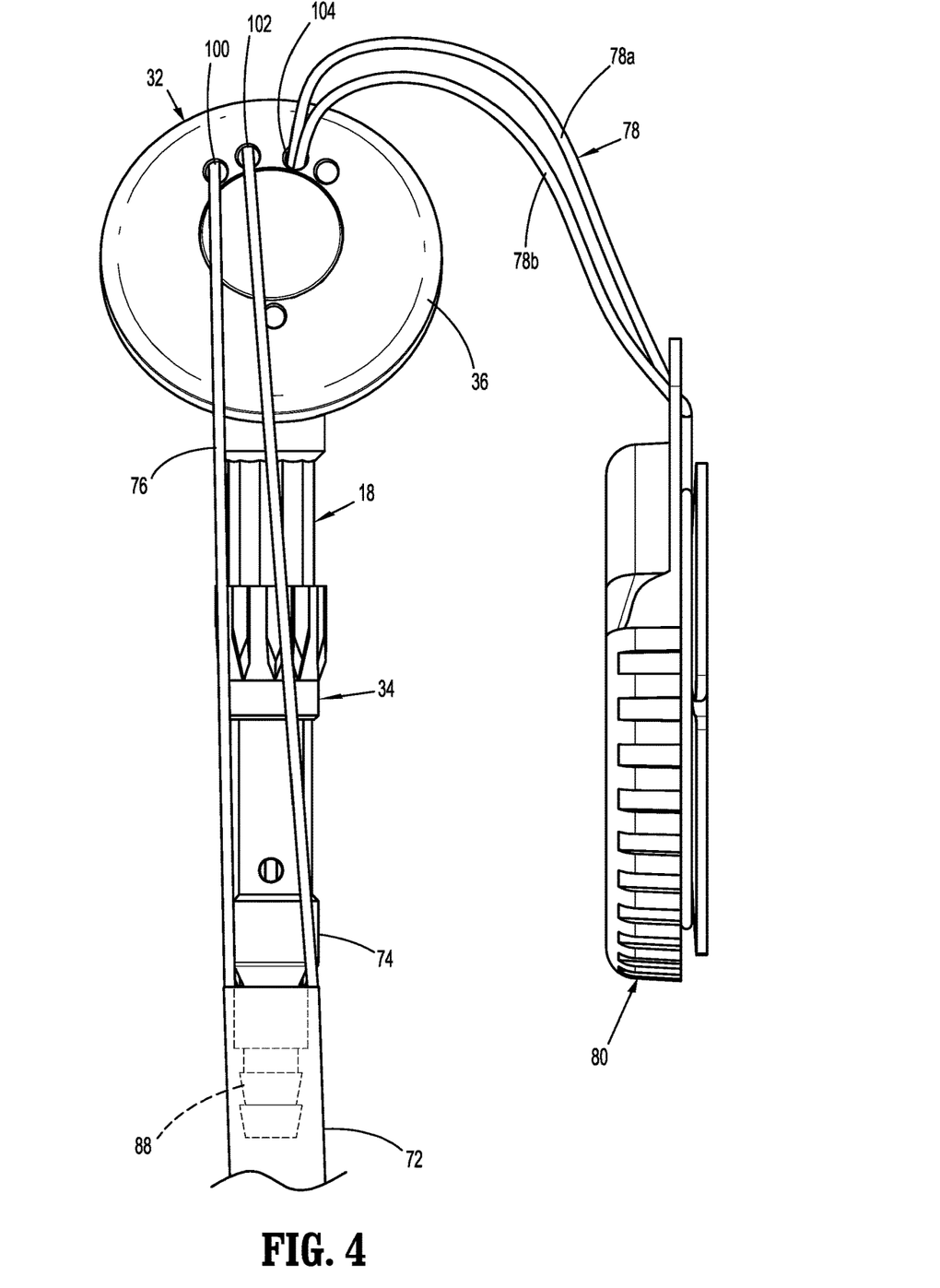
FIG. 4 is an enlarged view of the indicated area of detail shown in FIG. 3A.
Figure 5:
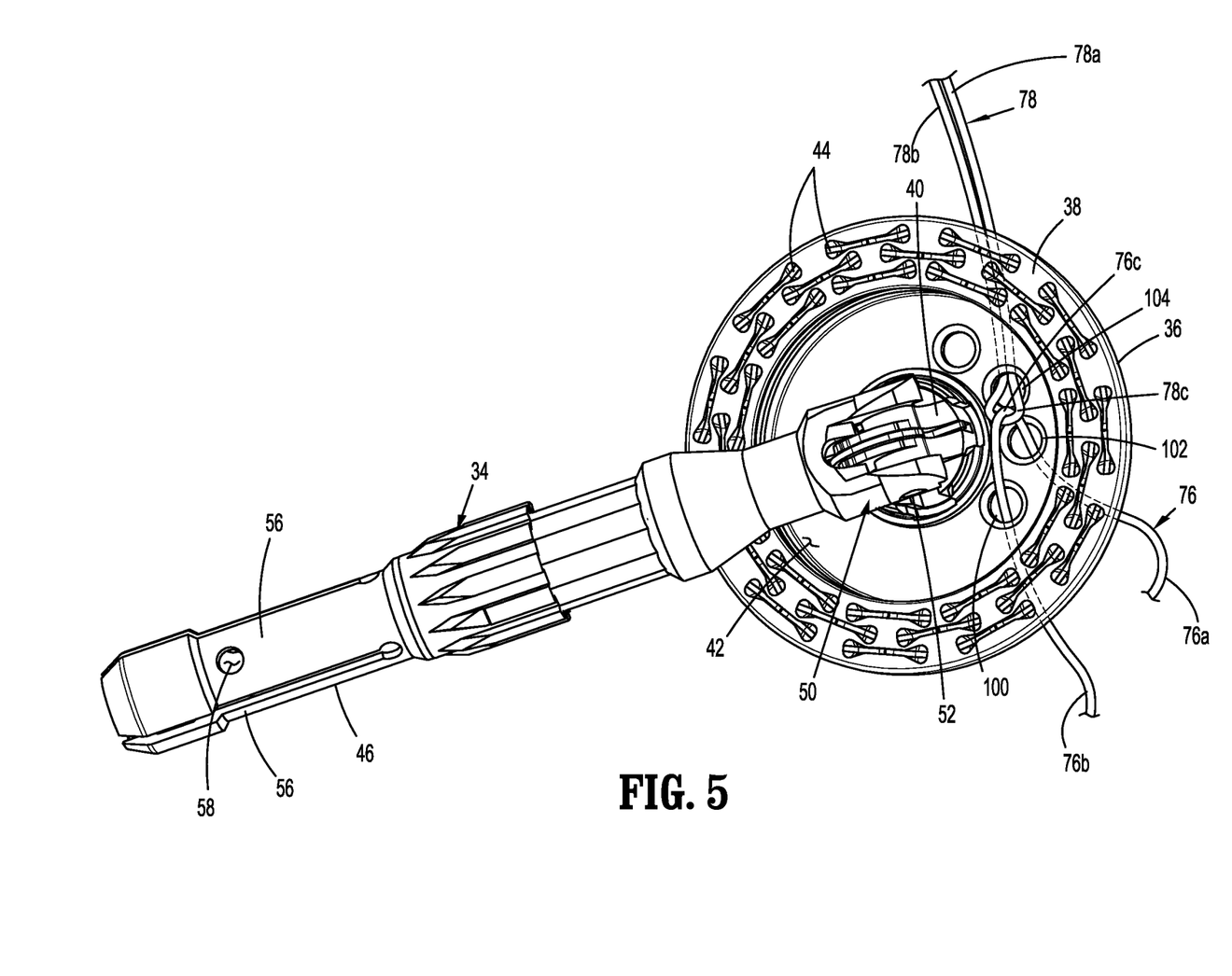
FIG. 5 is a side perspective view of the anvil shown in FIG. 4 showing the interconnection between the tie down suture and the guide suture.

FIG. 2 illustrates the anvil 18 which includes an anvil head 32 and a center rod 34. The anvil head 32 includes a body 36, an anvil plate 38 (FIG. 5), and a central post 40 (FIG. 5). The body 36 of the anvil head 32 defines a circular cavity 42 (FIG. 5) that receives the anvil plate 38. The anvil plate 38 has a circular configuration and defines a plurality of staple forming pockets 44 that are positioned about the circular cavity 42. The post 40 is secured to, or integrally formed with, the body 36 and is centrally positioned within the circular cavity 42.

The center rod 34 includes a proximal portion 46 and a distal portion 48. The proximal portion of the center rod 34 defines a clevis 50 (FIG. 5) that is secured to the post 40 of the anvil head 32 by a pivot member 52 (FIG. 5) to facilitate pivotable movement of the anvil head 32 in relation to the center rod 34 between tilted and operative positions. The proximal portion 46 of the center rod 34 includes flexible legs 56 that define a longitudinal bore 58 (FIG. 5) that receives a distal portion of the trocar assembly 30 (FIG. 1) to releasably secure the anvil 18 to the trocar assembly 30. The center rod 34 also includes a biasing mechanism that is positioned to urge the anvil head 32 initially the operative position and subsequently towards a second tilted position. U.S. Pat. Nos. 10,881,410, 10,779,833, and 9,861.367 disclose anvil assemblies suitable for use with the anvil delivery system to be described herein.

FIGS. 3A-5 illustrate the anvil delivery system coupled to the anvil 18. The anvil delivery system is shown generally as delivery system 70 and includes a flexible guide member 72, an adapter 74, a tie down suture 76, a retaining suture 78, and a reel 80. The flexible guide member 72 includes a blunt distal portion 82 and an open proximal portion 84. The adapter 74 (FIG. 3B) includes a central hub 86 that defines a through bore 86*a*, a distal connector 88, and a proximal connector 90. The distal connector 88 is received in the open proximal portion 84 of the flexible guide member 72 and includes ribs or teeth 92 that engage an inner wall of the flexible guide member 72 to frictionally secure the adapter 74 to the proximal portion 84 of the flexible guide member 72. The distal connector 88 also defines a through bore 88*a*. The proximal connector 90 of the adapter 74 is received within the proximal portion 46 of the center rod 34 of the anvil 18. In aspects of the disclosure, the proximal connector 90 of the adapter 74 includes a longitudinal rib 94 that is received between the flexible legs 56 of the center rod 34 to prevent rotation of the center rod 34 in relation to the adapter 74.

The tie down suture 76 includes first and second ends 76*a* and 76*b* and a central portion 76*c*. The tie down suture 76 is inserted through a first opening 100 in the body 36 of the anvil head 32 and exits a second opening 102 in the body 36 of the anvil head 32. The first and second ends 76*a* and 76*b* of the tie down suture 76 are compressed between the distal portion 88 of the adapter 74 and an inner surface of the flexible guide member 72 (FIG. 7) within the open proximal end 84 of the flexible guide member 72. The tie down suture 76 is maintained in tension to hold the anvil head 32 in the tilted position and to retain the proximal connector 90 of the adapter 74 within the proximal portion 46 of the center rod 34. In an alternate aspect of the disclosure, the tie down suture 76 can be inserted through the transverse bore 86*a* in the adapter 74 to secure the anvil head 32 of the anvil 18 to the adapter 74 and to secure the center rod 34 to the adapter 74.

The retaining suture 78 is inserted through a third opening 104 in the body 36 of the anvil head 32 and includes a central portion 78*c* that is wound about the central portion 76*c* of the tie down suture 76 (FIG. 5). The retaining suture 78 is inserted back through the third opening 104 such that the central portion 76*c* of the tie down suture 76 couples the retaining suture 78 to the anvil head 32 of the anvil 18. The retaining suture 78 includes first and second ends 78*a* and 78*b* that extend from the central portion 78*c* of the retaining suture 78 and are received within the reel 80. The reel 80 includes a length of retaining suture 78 and allows the retaining suture 78 to be selectively fed from the reel 80 as the anvil 18 is delivered to an anastomotic site within a body cavity, e.g., the stomach.

Figure 6:
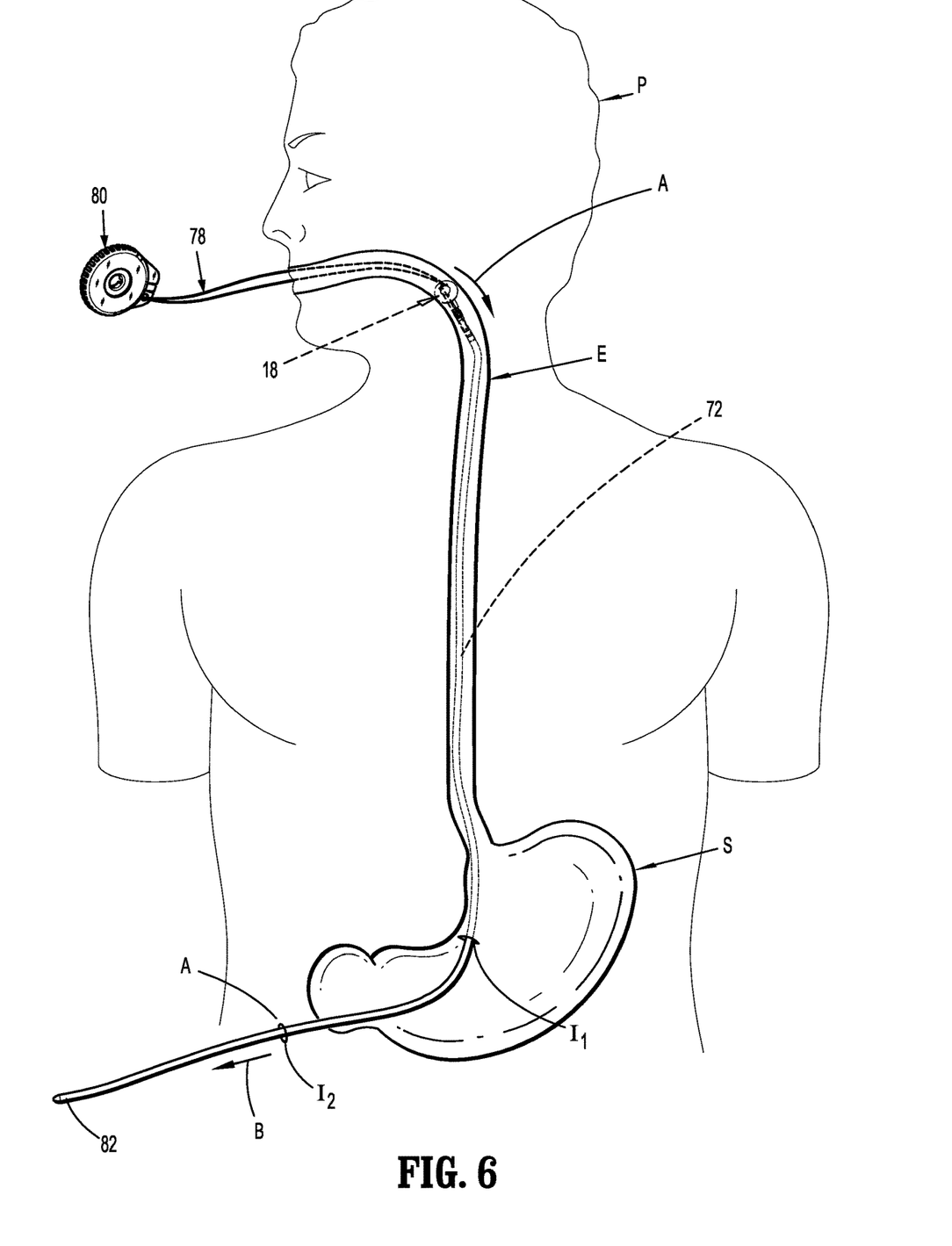
FIG. 6 is a view of the anvil and the anvil delivery system as the anvil is delivered to an anastomosis site within the body of a patient.

FIG. 6 illustrates delivery of the anvil to an anastomotic site, e.g., the stomach "S", of a patient "P" during an anastomosis procedure. During an anastomosis procedure, the flexible guide member 72 of the delivery system 70 is inserted through the patient's mouth "M" and fed through the esophagus "E" of the patient "P" in the direction of arrow "A" into the stomach "S". After the distal portion 82 of the flexible guide member 72 is received within the stomach "S", the distal portion 82 of the flexible guide member 72 is inserted through an incision "I₁" in the stomach "S" and through an incision "I₂" in the abdominal wall "A" of the patient "P" in the direction of arrow "B". When the distal portion 82 of the flexible guide member 72 is positioned externally of the patient "P", the distal portion 82 of the flexible guide member 72 is grasped by the clinician and pulled to move the anvil 18 through the esophagus "E" and into the stomach "S". It is noted that as the anvil 18 is fed into the patient "P", the retaining suture 78 is fed from the reel 80 into the esophagus "E" and stomach "S".

Figures 7, 8:
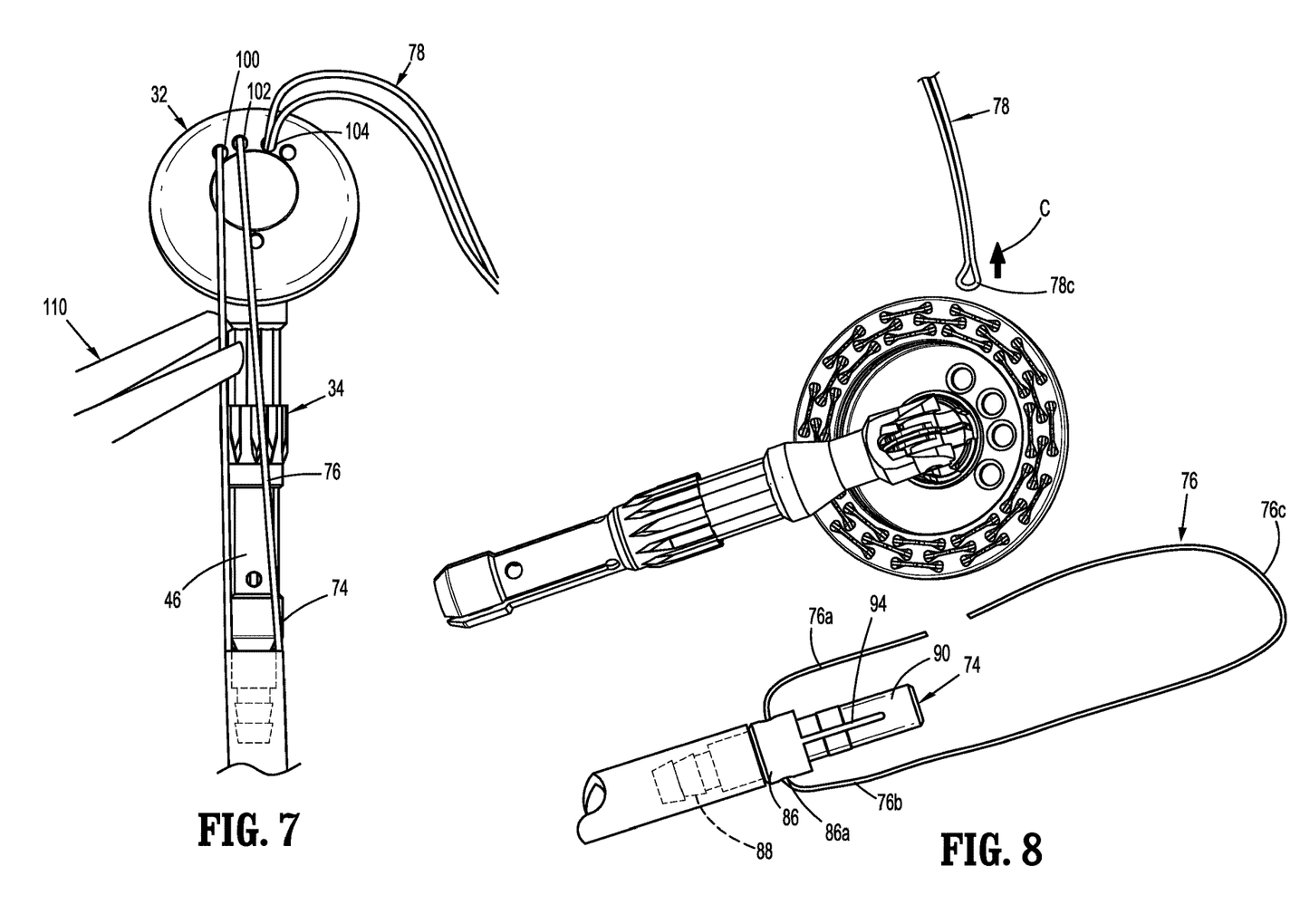
FIG. 7 is a side perspective view of the anvil and anvil delivery system as the anvil delivery system is released from the anvil.
FIG. 8 is a side perspective view of the anvil and delivery system assembly with the delivery system released from the anvil.

FIGS. 7 and 8 illustrate the anvil 18 as it would be in the stomach "S" of the patient "P". Once the anvil 18 is delivered to the stomach "S", the anvil 18 can be released from the adapter 74 of the delivery system 70 by cutting the tie down suture 76 with a scissor 110 and withdrawing the flexible guide member 72 from the patient "P" through the incisions "I₁" and "I₂" in the patient "P". As described above, the adapter 74 is fixedly coupled to the flexible guide member 72 of the delivery system 70. When the flexible guide member 72 is withdrawn from the patient "P", the adapter 74 and the tie down suture 76 which is clamped between the adapter 74 and the flexible guide member 72, are withdrawn from the patient "P". When the tie down suture 76 is withdrawn from the openings 100 and 102 of the body 36 of the anvil head 32 of the anvil 18, the tie down suture 76 is uncoupled from the retaining suture 78 to release the retaining suture 78 from the anvil head 32 (FIG. 8). At this point, the retaining suture 78 can be removed from the patient "P" in the direction of arrow "C" in FIG. 8 by pulling on the reel 80 to withdraw the retaining suture 78 through the esophagus "E".

Figure 9:
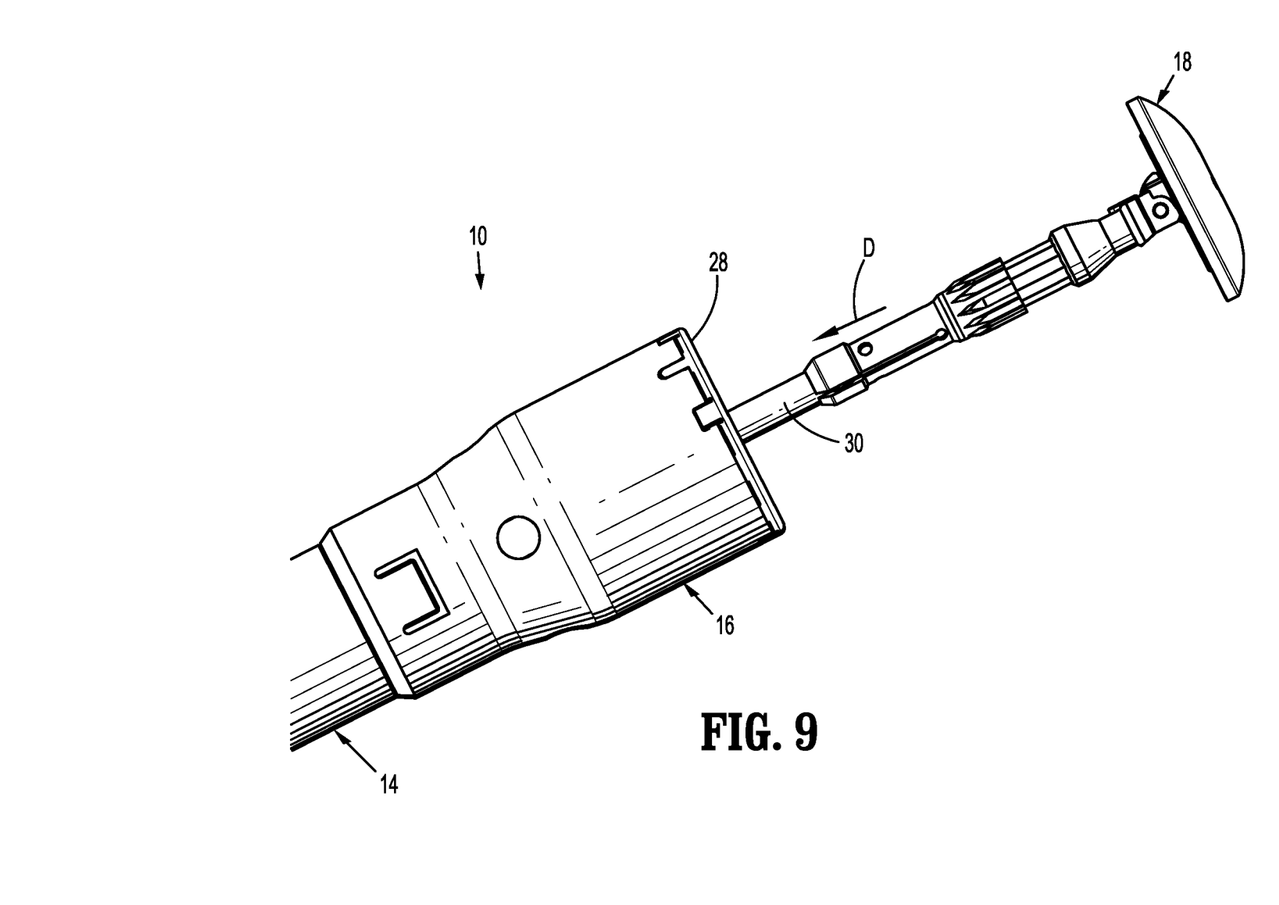
FIG. 9 is a side perspective view of the distal portion of the circular stapling device with the anvil attached to the anvil retainer of the circular stapling device.

After the delivery system 70 is removed from the patient "P", the anvil 18 can be coupled to the trocar assembly 30 of the stapling device 10 by inserting the trocar assembly 30 into the proximal portion 46 of the center rod 34 in the direction of arrow "D" in FIG. 9. At this point, the stapling device 10 can be operated in its customary manner to complete the anastomosis procedure without any concern of the retaining suture 78 becoming staples to the anastomotic site.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An anvil and delivery system assembly comprising:
    an anvil including an anvil head and a center rod, the anvil head secured to the center rod by a pivot member and movable between a first tilted position, an operative position, and a second tilted position; and
    a delivery system including a flexible guide member, an adapter, a tie down suture, and a retaining suture, the flexible guide member coupled to the center rod of the anvil with the adapter, the tie down suture secured to the anvil head and to the adapter to retain the anvil head in the first tilted position, and the retaining suture secured to the anvil head via the tie down suture such that release of the tie down suture from the anvil head automatically releases the retaining suture from the anvil head.

2. The anvil and delivery system assembly of claim 1, wherein the anvil head includes a body defining first and second openings, the tie down suture extending through the first opening in the anvil head and from the second opening of the anvil head to secure the tie down suture to the anvil head.

3. The anvil and delivery system assembly of claim 2, wherein the body of the anvil head defines a third opening, and the retaining suture extends into the third opening, is wound about the tie down suture, and extends back through the third opening to secure the retaining suture to the anvil head.

4. The anvil and delivery system assembly of claim 3, wherein the adapter includes a distal connector that is received within the flexible guide member to frictionally secure the adapter to the flexible guide member.

5. The anvil and delivery system assembly of claim 4, wherein the tie down suture includes first and second ends, the first and second ends compressed between the distal connector of the adapter and the flexible guide member.

6. The anvil and delivery system assembly of claim 5, wherein the delivery system includes a reel, and a portion of the retaining suture is supported within the reel and can be selectively fed from the reel.

7. The anvil and delivery system assembly of claim 4, wherein the distal connector includes ribs that engage the flexible guide member to secure the adapter within the flexible guide member.

8. The anvil and delivery system assembly of claim 4, wherein the adapter includes a proximal connector that is received within the center rod of the anvil.

9. The anvil and delivery system assembly of claim 1, wherein the center rod includes a distal portion that is coupled to the anvil head by the pivot member and a proximal portion that includes flexible legs that define a longitudinal bore, the longitudinal bore dimensioned to releasably receive a trocar of a stapling device to releasably secure the anvil to the stapling device.

10. An anvil and delivery system assembly comprising:
an anvil including an anvil head and a center rod, the anvil head secured to the center rod by a pivot member and movable between a tilted position and an operative position; and
a delivery system including a flexible guide member, a tie down suture, and a retaining suture, the flexible guide member coupled to the center rod of the anvil, the tie down suture secured to the anvil head and to the flexible tube to retain the anvil head in the tilted position, and the retaining suture secured to the anvil head via the tie down suture such that release of the tie down suture from the anvil head automatically releases the retaining suture from the anvil head.

11. The anvil and delivery system assembly of claim 10, wherein the anvil head includes a body defining first and second openings, the tie down suture extending through the first opening in the anvil head and from the second opening of the anvil head to secure the tie down suture to the anvil head.

12. The anvil and delivery system assembly of claim 11, wherein the body of the anvil head defines a third opening, and the retaining suture extends into the third opening, is wound about the tie down suture, and extends back through the third opening to secure the retaining suture to the anvil head.

13. The anvil and delivery system assembly of claim 12, wherein the center rod includes a distal portion that is coupled to the anvil head by the pivot member and a proximal portion that includes flexible legs that define a longitudinal bore, the longitudinal bore dimensioned to releasably receive a trocar of a stapling device to releasably secure the anvil to the stapling device.

14. The anvil and delivery system assembly of claim 13, wherein the proximal connector of the adapter includes a rib that is received between the flexible legs of the center rod to prevent rotation of the center rod in relation to the adapter.

15. The anvil and delivery system assembly of claim 10, further including an adapter coupling the flexible guide member to the center rod of the anvil.

16. The anvil and delivery system assembly of claim 15, wherein the adapter includes a distal connector that is received within the flexible guide member to frictionally secure the adapter to the flexible guide member.

17. The anvil and delivery system assembly of claim 16, wherein the tie down suture includes first and second ends, the first and second ends compressed between the distal connector of the adapter and the flexible guide member.

18. The anvil and delivery system assembly of claim 17, wherein the delivery system includes a reel, and a portion of the retaining suture is supported within the reel and can be selectively fed from the reel.

19. The anvil and delivery system assembly of claim 16, wherein the distal connector includes ribs that engage the flexible guide member to secure the adapter within the flexible guide member.

20. The anvil and delivery system assembly of claim 19, wherein the adapter includes a proximal connector that is received within the center rod of the anvil.

\* \* \* \* \*